(12) United States Patent
Kaivosoja et al.

(10) Patent No.: US 12,311,195 B2
(45) Date of Patent: May 27, 2025

(54) THERANOSTIC LASER SYSTEM

(71) Applicant: Modulight, Inc., Tampere (FI)

(72) Inventors: Visa Kaivosoja, Tampere (FI); Lasse Orsila, Tampere (FI); Petteri Uusimaa, Tampere (FI)

(73) Assignee: Modulight Corporation, Tampere (FI)

( * ) Notice: Subject to any disclaimer, the term of this patent is extended or adjusted under 35 U.S.C. 154(b) by 95 days.

(21) Appl. No.: 17/392,399

(22) Filed: Aug. 3, 2021

(65) Prior Publication Data

US 2023/0038534 A1 Feb. 9, 2023

(51) Int. Cl.
*A61N 5/067* (2006.01)
*A61N 5/06* (2006.01)

(52) U.S. Cl.
CPC ............ *A61N 5/067* (2021.08); *A61N 5/062* (2013.01); *A61N 2005/0626* (2013.01); *A61N 2005/063* (2013.01)

(58) Field of Classification Search
CPC .................. A61N 5/067; A61N 5/062; A61N 2005/0626; A61N 2005/063; A61B 2017/00057; A61B 18/22
See application file for complete search history.

(56) References Cited

U.S. PATENT DOCUMENTS

| | | | | |
|---|---|---|---|---|
| 4,889,129 A * | 12/1989 | Dougherty | ........... | A61N 5/0601 606/4 |
| 10,588,514 B1 * | 3/2020 | Shang | ................. | A61B 5/6851 |
| 10,594,112 B1 * | 3/2020 | Shang | ................. | A61B 5/0071 |
| 2013/0123648 A1 * | 5/2013 | Stampoulidis | ......... | A61N 5/062 600/478 |
| 2017/0021189 A1 | 1/2017 | Thompson et al. | | |
| 2018/0113247 A1 * | 4/2018 | Rose | ..................... | G02B 6/262 |
| 2020/0256777 A1 * | 8/2020 | Lin | ..................... | G01N 15/1459 |
| 2021/0172864 A1 * | 6/2021 | McCurdy | ............. | G01N 33/493 |

FOREIGN PATENT DOCUMENTS

| | | |
|---|---|---|
| AU | 2020100961 A4 | 7/2020 |
| CN | 109331345 B | 11/2019 |
| CN | 111991704 B | 12/2022 |

OTHER PUBLICATIONS

European Patent Office, Written Opinion of the International Searching Authority, mailed Nov. 7, 2022, 3 pages.

* cited by examiner

*Primary Examiner* — Carl H Layno
*Assistant Examiner* — Aya Ziad Bakkar
(74) *Attorney, Agent, or Firm* — Ziegler IP Law Group LLC

(57) ABSTRACT

A theranostic laser system for light-activated drug delivery and monitoring. The system includes a light source, a light receiver and a coupler for simultaneously coupling a first optical delivery fiber to the light source for transmitting one or more first downstream light signals from the light source to the first optical delivery fiber and to the light receiver for transmitting one or more first upstream light signals from the first optical delivery fiber to the light receiver.

13 Claims, 2 Drawing Sheets

THERANOSTIC LASER SYSTEM

FIELD

The aspects of the disclosed embodiments relate to a theranostic laser system, which can be used to facilitate light-activated drug delivery. In particular, it may be utilized in the field of oncology, photodynamic therapy, immunotherapy, and/or biomedical imaging.

BACKGROUND

Medical lasers are used, for example, in operating room and sterile conditions. Therapeutic or hard tissue illumination provided by the medical laser may be combined with treatment monitoring functions to provide a theranostic medical device. It would be beneficial to improve drug delivery process with theranostic medical devices.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

The solutions disclosed herein combine functionalities of therapeutic laser systems with some properties of diagnostic/monitoring devices. The solutions can be used with light-activated drug delivery constructs, such as nano-constructs. These may comprise or consist of a carrier, such as a liposome, an encapsulated drug and/or targeting component within the carrier, and a light-activated component/photosensitizer. A drug delivery system can be configured for simultaneously facilitating the actuation of a therapeutic effect and monitoring various processes during such treatment by utilizing fluorescence and/or other optical imaging solutions for components of the drug-delivery construct.

It is disclosed a low-invasive solution which can be used for not only inducing the multi-phase therapeutic drug delivery effect but additionally or alternatively for monitoring multiple processes happening during photodynamic therapy (PDT), photochemotherapy treatment or other light-utilizing treatment modality. The solutions allow utilization of standard light-activation illumination fibers also for monitoring interstitial processes eliminating the need of introducing any unnecessary foreign objects to the tissue to minimize mechanical stress caused to the tissue.

The disclosed solutions may be used in oncology to allow a clinician more precisely illuminate a tumor as a whole and monitor progress during a treatment. This functionality may markedly increase the odds for success for light-activated therapies, in particular by allowing real-time feedback from the tumor environment. The previously introduced treatment monitoring solutions for PDT, photoimmunotherapy (PIT) or other light-activated drug delivery methods are typically based on using separate probes or cameras for optical monitoring purposes. The disclosed solutions may be utilized with an all-fiber single multi-purpose probe for treatment delivery and monitoring and allow simultaneous treatment activation and monitoring real-time and independent of each other without separate switching between the different modalities (in particular of treatment and monitoring). The solutions further support separation of different optical signals, which may be represented by different wavelengths, at a monitoring device by applying a wave-length-sensitive detection unit.

According to an aspect, a theranostic laser system for light-activated drug delivery is disclosed. The system comprises a light source for providing downstream light signals for actuating and/or monitoring drug delivery, a light receiver for receiving upstream light signals for monitoring the drug delivery, and a coupler for simultaneously coupling a first optical delivery probe, such as an optical delivery fiber, to the light source for transmitting one or more first downstream light signals from the light source to the first optical delivery probe, and to the light receiver for transmitting one or more first upstream light signals from the first optical delivery probe to the light receiver.

In an embodiment, the light source comprises a first laser module coupled and dedicated to the coupler for transmitting the first downstream light signals to the first optical delivery probe.

In an embodiment, the system comprises a dedicated shutter coupled between the light receiver and the coupler for blocking the first upstream light signals transmitted from the coupler.

In an embodiment, the system is configured for obtaining a measurement of a dark spectrum with the dedicated shutter closed for adjusting a subsequent measurement of the upstream signal to improve signal-to-noise ratio using the measurement of the dark spectrum.

In an embodiment, the system comprises a receiver coupler coupled between the light receiver and the coupler for bundling upstream light signals from two or more couplers.

In an embodiment, the receiver coupler includes a filter that is configured to attenuate one or more wavelengths provided by the light source and/or facilitate transmission of one or more monitoring signals.

In an embodiment, the system comprises a mode-mixing element for coupling the light receiver to the receiver coupler for homogenizing a signal provided to the light receiver from the filter.

In an embodiment, the mode-mixing element is a non-circular light guide such as a square fiber, a hexagonal fiber, a square rod or a hexagonal rod.

In an embodiment, the system comprises a second coupler for simultaneously coupling a second optical delivery probe, such as an optical delivery fiber, to the light source for transmitting second downstream light signals from the light source to the second optical delivery probe, and to the light receiver for transmitting one or more second upstream light signals from the second optical delivery probe to the light receiver.

In an embodiment, the coupler is a passive two-way fiber coupler.

In an embodiment, the light receiver is a photodetector or a spectrometer or a combination of a wavelength de-multiplexing unit and one or more photodetectors.

In an embodiment, the light source and the light receiver are communicatively connected to a signal processing unit for collecting, analyzing and processing data for further use.

In an embodiment, the signal processing unit is communicatively connected to a remote data processing unit that collects the data from the treatment, analyses it and delivers guidance for the drug delivery.

In an embodiment, the signal processing unit is configured for using algorithms based on machine learning and/or artificial intelligence for analyzing the data from one or more earlier treatments and delivers guidance for the drug delivery.

It is to be understood that the aspect and the embodiments described above may be used in any combination with each other. Several of the embodiments may be combined together to form a further embodiment of the present disclosure.

The disclosed system allows simultaneous multi-channel and multi-wavelength optical tissue monitoring (e.g. fluorescence, reflectance, and/or absorption) with illumination. It allows multiple treatment and/or monitoring signals to be transmitted using a single channel such as a single optical probe/fiber. It thereby also allows increased flexibility in customization of treatment and/or monitoring. There is no need for manual or sequential measurement procedure between channels. Instead, two or more channels can be freely combined for simultaneous measurement. Illumination, such as treatment and/or monitoring illumination, can be performed at the same time as measurement, such as a monitoring measurement. The system can be operated with automatic multichannel measurement.

Additionally, the disclosed system allows channel specific filtering. It may be provided with compact all-fiber robust design. Cross-talk between measurement channels may be mitigated or removed altogether. Multiple wavelength excitation may be used, for example for fluorescence monitoring. Multiple wavelength illumination and/or measurement may also be use. Multiple illumination and/or measurement application probes/fibers may still be used. The system may also be configured for local and/or remote data storage and/or analysis. The system may be configured for performing this automatically.

The theranostic laser system may be used for both inducing a therapeutic effect of a treatment and monitor different processes taking place during the treatment. It may be configured for performing this automatically. Light delivery for treatment and monitoring may utilize the same optical probes, such as optical fibers, for both processes without need to insert separate monitoring devices around the treated tissue area or switch between treatment probes and monitoring probes at selected locations. The system may comprise one or more lasers with one or more wavelengths for a drug delivery construct to activate treatment or excite an optical monitoring process. Different components of a drug delivery construct can be optically monitored freely in parallel without need for switching between different functions of each delivery channel. Multiple illumination wavelengths can be coupled into single optical fiber probe that is inserted into tissue without any physical or optical switching between different functions. This makes it possible to do treatment and monitoring simultaneously and thus get real-time information about the treatment progress. This information about different interstitial processes during the treatment can be collected to a remote processing system such as a cloud. It can be analyzed locally or remotely for treatment decision making. The very same probes inserted into the tissue can be also used for collecting optical signals, possibly with different wavelengths, from the tissue to monitor different drug delivery processes in-situ when delivering the treatment.

BRIEF DESCRIPTION OF THE DRAWINGS

The accompanying drawings, which are included to provide a further understanding and constitute a part of this specification, illustrate examples and together with the description help to explain the principles of the disclosure. In the drawings.

Like references are used to designate equivalent or at least functionally equivalent parts in the accompanying drawings.

DETAILED DESCRIPTION

The detailed description provided below in connection with the appended drawings is intended as a description of examples and is not intended to represent the only forms in which the example may be constructed or utilized. However, the same or equivalent functions and structures may be accomplished by different examples.

Figure 1:
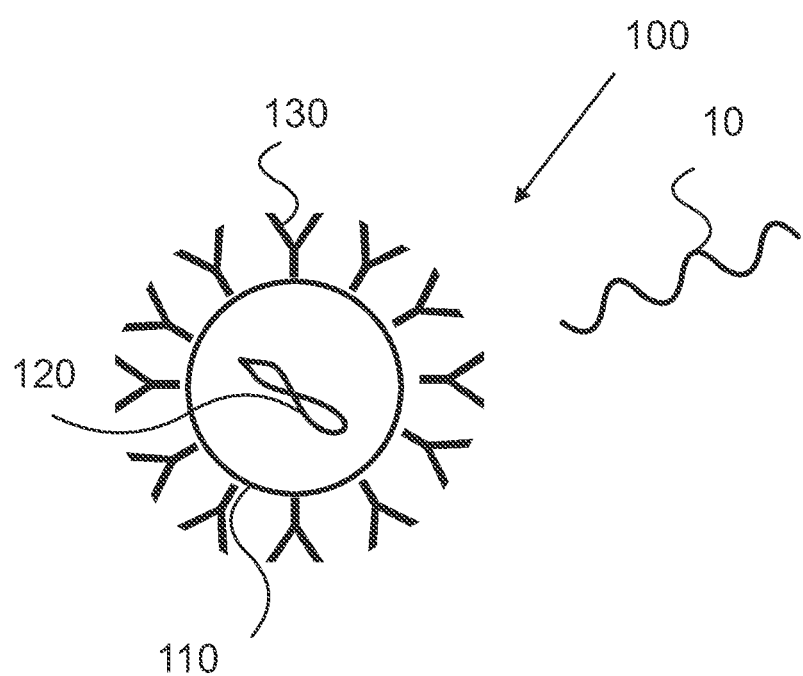
FIG. 1 illustrates a drug-delivery construct according to an example.

FIG. 1 shows an example of a drug-delivery construct 100 for multi-phase drug delivery. The drug delivery construct may be a nano-construct. It may comprise or consist of a carrier 110, one or more drugs and/or targeting components 120 within the carrier, and one or more light-activated components, such as photosensitizers. The carrier may comprise or consist of a liposome, such as a nanoliposome. It can encapsulate the one or more drugs and/or targeting components. The one or more drugs may comprise or consist of, for example, one or more chemotherapeutic drugs, such as Irinotecan. One or more elements 130 may be coupled to the carrier for multi-phase drug-delivery. These elements may comprise antibodies and/or photosensitizers. The antibodies may be, for example, EGFR-targeted antibodies such as Cetuximab. The photosensitizer may be, for example benzoporphyrin derivative (BPD). The photosensitizers may be coupled to the antibodies, for example on the surfaces of the antibodies. The one or more elements may thereby comprise antibody-conjugated photosensitizers, e.g. BPD+Cetuximab. The drug delivery may be actuated by light 10 such as laser light, for example near-infrared laser light. Actuation of drug delivery, wherever referred, may comprise activation of a drug, such as a photoactive drug, and/or a photosensitizer, for example by a photodynamic reaction. Additionally or alternatively, it may comprise enhancing the efficacy of a drug. Monitoring of drug delivery, wherever referred, may comprise, for example, actuating response from one or more (monitoring) targets such as dyes, fluorescence labels and/or photosensitizers and/or receiving any such response(s). Alternatively or additionally, monitoring may comprise activating a characteristic optical response, like fluorescence, reflectance or Raman scattering signal or alike, from tissue itself, and/or receiving any such response.

All of the aforementioned actuating and monitoring alternatives may be facilitated by delivering light to the tissue through an optical probe, such as an optical fiber. In particular, the same optical probe may be used for any combination of the alternatives. Two or more of the alternatives, regardless of whether they involve actuating or monitoring the drug delivery, may be performed simultaneously utilizing the same probe.

Figure 2:
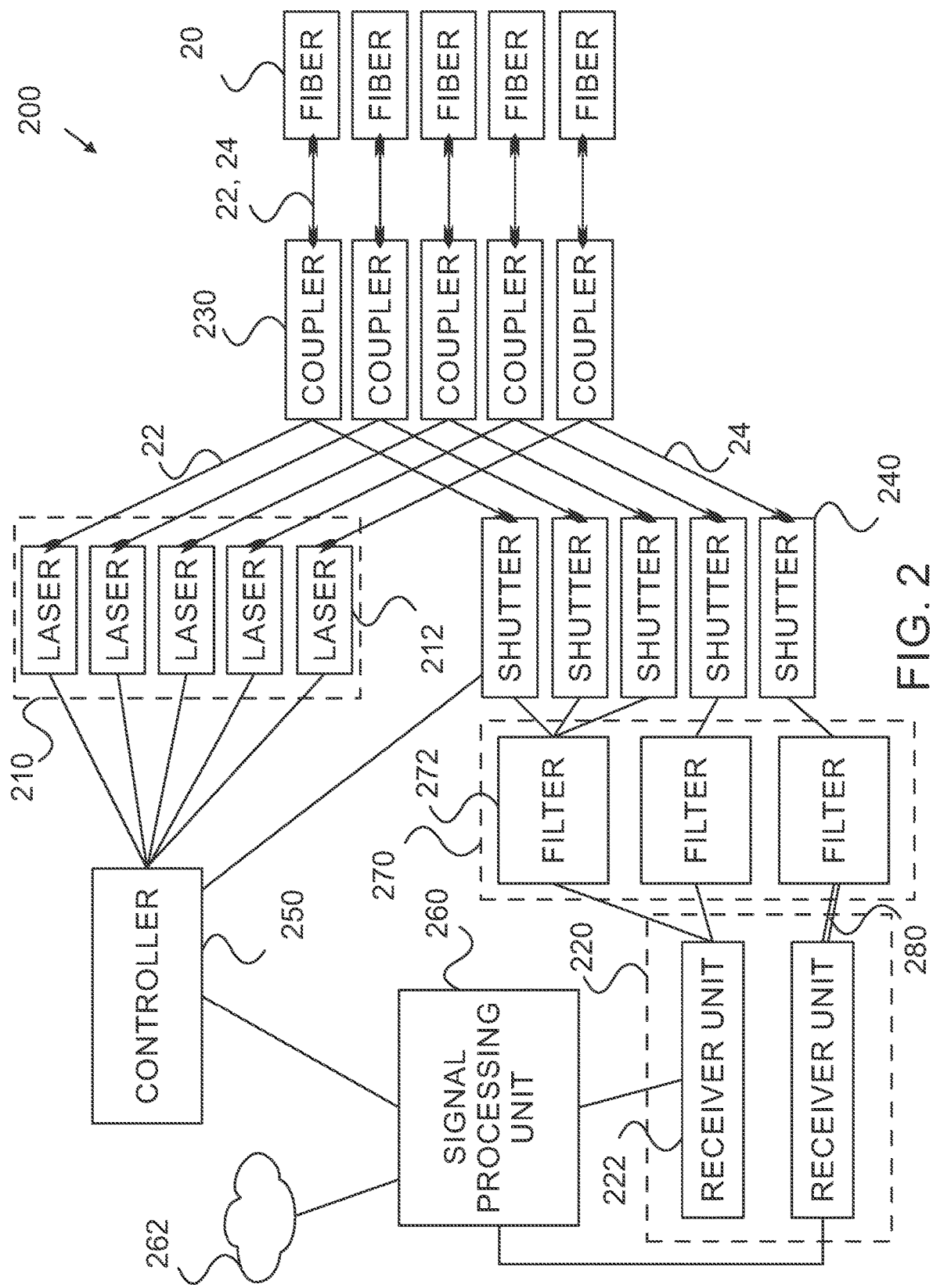
FIG. 2 schematically illustrates a system according to an example.

FIG. 2 shows an example of a system 200. The system is a laser system, such as a theranostic laser system, which may be used for medical treatment and/or monitoring, in particular for facilitating light-activated drug delivery. The drug delivery may be multi-phase drug deliver comprising two or more treatment and/or monitoring phases. For example, the drug delivery may involve providing the drug delivery construct 100 described above to a subject, such as a patient. The system may thereby be configured for actuating, e.g. by light activation, and monitoring the delivery of the drug-delivery construct to the subject. The system may be configured for oncology, photodynamic therapy, photoimmunotherapy and/or biomedical imaging.

The system 200 may comprise a light source 210, which may be configured for providing downstream light signals 22 for actuating and/or monitoring drug delivery. The light source may comprise one or more laser modules 212, such as infrared laser modules, for providing the downstream light signals. The downstream light signals may be provided as light pulses and/or as continuous waves. The system may also comprise a light receiver 220, which may be configured for receiving upstream light signals 24 for monitoring the drug delivery. The light receiver may comprise one or more receiver units 222, such as spectrometers and/or photodetectors, for this purpose. The receiver unit may also be a combination of a wavelength demultiplexing unit and one or more photodetectors. The light receiver, or the receiver unit(s), may comprise a wave-length-sensitive detection unit for distinguishing received light signals based on their wavelength. The wavelength-sensitive detection unit may be configured for simultaneously monitoring two or more different wavelengths received from the optical delivery probe(s) for monitoring drug delivery.

The system 200 may comprise one or more couplers 230, which may be fiber couplers, such as passive two-way fiber couplers. Each of the one or more couplers may be configured for simultaneously coupling an optical delivery probe 20, such as an optical delivery fiber, to the light source 210 for transmitting one or more first downstream light signals from the light source to the optical delivery probe and to the light receiver for transmitting one or more first upstream light signals from the optical delivery probe to the light receiver. The couplers can thus be separate so that each coupler is dedicated to its own probe. Each coupler and each probe may provide a separate measurement channel for the system. The system may also comprise the optical delivery probe(s) or they may be provided separately.

The laser module(s) 212 of the light source 210 may be coupled and dedicated to the coupler(s) for transmitting the downstream light signals 22 to their corresponding optical delivery probe 20. Each of the laser modules can thus be dedicated to a single coupler and, through it, to a single probe. Each of the laser modules may be configured for providing light having a fixed wavelength or for providing light of multiple different wavelengths. The system 200 may comprise a dedicated shutter 240 for each of the couplers 230, and thereby also for each the optical delivery probes 20. The shutter may be coupled, indirectly or directly, between the light receiver 220 and the corresponding coupler for blocking the upstream light signals 24 transmitted from the coupler. This allows the receipt of light from each of the probes to be individually controlled. The system may comprise a controller 250, which may be coupled to each of the shutters for controlling the shutter, e.g. between, at least, an open and a closed position. The controller may be configured for altering the state of the shutter(s) automatically.

The system 200 may also comprise a controller 250, which may be the controller described above, coupled to the light source 210, for example to each of the laser modules 212, for controlling the provision of the downstream light signals. This may include controlling any of the timing, the amplitude, the wavelength and the pulse length of the downstream light signals, alone or in any combination. The controller may be configured for altering provision of the downstream light signals.

The system 200 may comprise a signal processing unit 260, such as a computer, e.g. a personal computer (PC). It may be configured for any of storing, providing and analyzing data and/or instructions, such as measurement data and/or instructions, pertaining to the drug delivery, alone or in any combination. The controller(s) 250 may comprise or be coupled to the signal processing unit, for example for receiving operating instructions. The signal processing unit may be a local or a remote signal processing unit or a combination of the two. It may be coupled to a remote data processing unit 262, such as cloud processing unit, for the storing, providing and analyzing data and/or instructions. The signal processing unit may thus be communicatively connected to the remote data processing unit, which may be configured for collecting data from the drug delivery, for example data from treatment. The connection may be made by any means available to a person skilled in the art of electronic communications, for example through Ethernet, wireless local area network and/or cellular network connection. The signal processing unit may be configured to analyze the data and/or deliver guidance, such as operating instructions, for the drug delivery, for example to the controller 250, and/or for the light source 210 and/or the light receiver 220. The light source and/or the light receiver may be communicatively connected to the signal processing unit, for example directly and/or through the controller, for example for any of collecting, analyzing and processing data for further use. The signal processing unit may be configured for using algorithms based on machine learning and/or artificial intelligence for analyzing the data from one or more earlier treatments and delivering guidance, such as operating instructions for the light source and/or the light receiver, for the drug delivery. This may also include also guidance for a drug delivery unit, which may be configured for continuously or repeatedly delivering one or more drugs, for example the drug delivery construct 100, to a subject, such as a patient, during the operation of the system. The drug delivery unit may be provided as a part of the system or separately. The drug delivery unit may be configured for delivering the drug(s) to the subject, for example via IV (intravenously) and/or IP (intraperitoneally). The drug delivery unit may be configured for adjusting the dosage of the drug, for example automatically, e.g. based on instructions provided by the controller 250 and/or the signal processing unit 260.

The system 200 may be configured for obtaining a measurement of a dark spectrum with any or all of the dedicated shutters 240 closed. The system may be configured for adjusting a subsequent measurement of the upstream signal to improve signal-to-noise ratio using the measurement of the dark spectrum. The system may be configured for performing the measurement and/or adjusting the subsequent measurement(s) automatically. The controller 250 and/or the signal processing unit 260 may be configured for any of said purposes.

The system 200 may comprise a receiver coupler 270 coupled between the light receiver 220 and the coupler 230 for bundling upstream light signals 24 from two or more couplers. Correspondingly, the bundled upstream light signals may be provided as a bundled signal to the light receiver, or to one or more receiver units 222 thereof. The receiver coupler may be coupled between the light receiver and the shutter(s), or any or all of the shutters may be arranged as part of the receiver coupler. The receiver coupler may comprise one or more filters. These may be configured to attenuate one or more wavelengths provided by the light source and/or facilitate transmission of one or more monitoring signals, for example corresponding to one or more fluorescence wavelengths. A single filter may be coupled to one or more couplers 230, and thereby to one or more optical delivery probes 20. The system may comprise one or more mode-mixing elements 280 for coupling the light receiver to the receiver coupler. These may be configured for homogenizing a signal provided to the light receiver from the filter 272. The one or more mode-mixing elements may comprise or consist of one or more non-circular light guides such as square fibers, hexagonal fibers, square rods and/or hexagonal rods.

A particular solution has a system 200 comprising a cloud-connected PC 260, laser and shutter controllers 250, spectrometer(s)/photodetectors 220, laser modules 212, fiber couplers 230, fiber shutters 240 and filters 272.

One or more channels with individual laser modules 212 may be coupled through a coupler, such as a lens coupler, into an optical delivery probe such as an application fiber. Light coming back from the probe can be collected through a coupler, such as a fiber coupler. Here, the lens coupler and the fiber coupler can now be integrated as a single two-way coupler 230, where a first path is for the downstream light signals 22 from the light source 210 to the optical delivery probe 20 and the second path is for the upstream light signals 24 from the optical delivery probe to the light receiver 220. Light collected from the probes/fibers can be guided through individually controllable shutters 240 and bundled to a spectrometer through an in-line filter 272. The filter can be shared between all channels or there can be more than one filter coupled with one or more channels. Filters can be configured, for example, to attenuate laser emission wavelengths and pass through fluorescence wavelengths. Mode-mixing fiber before spectrometer/photodetector can be used to homogenize the signal.

Light guiding via probes such as fibers and fiber bundles allows making the design robust and flexible for customization. Dark spectra can be measured, for example, by keeping all shutters closed. This measurement can be removed from other measurements to achieve better signal-to-noise ratio. Measurement data can be stored and analyzed locally on PC and/or sent to cloud for storage and analysis. Raw or processed data can be visualized locally on device display or via cloud service. Cloud-based data collection system enables high throughput remote processing and analysis and comparison to existing other field data for treatment session optimization.

The system 200 allows real-time monitoring of drug delivery (in contrast to prescribed intervals) and/or monitoring multiple dyes or photosensitizers (e.g. with multiple wavelengths). It has applicability for multiphase treatments and no need to use switches and/or shutters or separate fibers for detection channels. A single laser source can also be used both as a treatment beam and for monitoring, for example for detection and/or activation monitoring excitation light such as fluorescence light. The system can be used for light dosimetry. It may be used for in-situ monitoring of tissue. It also allows collecting spectral point information at several locations in a tissue simultaneously. Monitoring may be performed with a single spectrometer, in contrast to using multiple ones. Monitoring may be based on spectral information. The solutions may be implemented as multi-channel and/or multi-wavelength solutions.

The system as described above may be implemented in software, hardware, application logic or a combination of software, hardware and application logic. The application logic, software or instruction set may be maintained on any one of various conventional computer-readable media. A "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer. The examples can store information relating to various processes described herein. This information can be stored in one or more memories, such as a hard disk, optical disk, magneto-optical disk, RAM, and the like. One or more databases can store the information used to implement the embodiments. The databases can be organized using data structures (e.g., records, tables, arrays, fields, graphs, trees, lists, and the like) included in one or more memories or storage devices listed herein. The databases may be located on one or more devices comprising local and/or remote devices such as servers. The processes described with respect to the embodiments can include appropriate data structures for storing data collected and/or generated by the processes of the devices and subsystems of the embodiments in one or more databases.

All or a portion of the embodiments can be implemented using one or more general purpose processors, microprocessors, digital signal processors, micro-controllers, and the like, programmed according to the teachings of the embodiments, as will be appreciated by those skilled in the computer and/or software art(s). Appropriate software can be readily prepared by programmers of ordinary skill based on the teachings of the embodiments, as will be appreciated by those skilled in the software art. In addition, the embodiments can be implemented by the preparation of application-specific integrated circuits or by interconnecting an appropriate network of conventional component circuits, as will be appreciated by those skilled in the electrical art(s). Thus, the embodiments are not limited to any specific combination of hardware and/or software.

The different functions discussed herein may be performed in a different order and/or concurrently with each other.

Any range or device value given herein may be extended or altered without losing the effect sought, unless indicated otherwise. Also any example may be combined with another example unless explicitly disallowed.

Although the subject matter has been de-scribed in language specific to structural features and/or acts, it is to be understood that the subject matter defined in the appended claims is not necessarily limited to the specific features or acts de-scribed above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The term 'comprising' is used herein to mean including the method, blocks or elements identified, but that such blocks or elements do not comprise an exclusive list and a method or apparatus may contain additional blocks or elements.

Numerical descriptors such as 'first', 'second', and the like are used in this text simply as a way of differentiating between parts that otherwise have similar names. The numerical descriptors are not to be construed as indicating any particular order, such as an order of preference, manufacture, or occurrence in any particular structure.

Although the aspects of the disclosed embodiments have been the described in conjunction with a certain type of apparatus and/or method, it should be understood that the aspects of the disclosed embodiments are not limited to any certain type of apparatus and/or method. While the present disclosures have been described in connection with a number of examples, embodiments and implementations, the present disclosures are not so limited, but rather cover various modifications, and equivalent arrangements, which fall within the purview of the claims. Although various examples have been described above with a certain degree of particularity, or with reference to one or more individual embodiments, those skilled in the art could make numerous alterations to the disclosed examples without departing from the scope of this specification.

The invention claimed is:

1. A theranostic laser system for light-activated drug delivery, the system comprising:
    a light source for providing downstream light signals for actuating and/or monitoring drug delivery;
    a light receiver for receiving upstream light signals for monitoring the drug delivery;
    a first coupler for simultaneously coupling a first optical delivery fiber:
        to the light source for transmitting one or more first downstream light signals from the light source to the first optical delivery fiber, and
        to the light receiver for transmitting one or more first upstream light signals from the first optical delivery fiber to the light receiver,
        wherein the first upstream and downstream light signals occur simultaneously without switching by the first coupler; and
    a second coupler for simultaneously coupling a second optical delivery fiber:
        to the light source for transmitting second downstream light signals from the light source to the second optical delivery fiber, and
        to the light receiver for transmitting one or more second upstream light signals from the second optical delivery fiber to the light receiver,
        wherein the second upstream and downstream light signals occur simultaneously without switching by the second coupler;
    wherein the first and second couplers are separate and the first coupler is dedicated to the first optical delivery fiber and the second coupler is dedicated to the second optical delivery fiber.

2. The system according to claim 1, wherein the light source comprises a first laser module coupled and dedicated to the coupler for transmitting the first downstream light signals to the first optical delivery fiber.

3. The system according to claim 1, comprising a dedicated shutter coupled between the light receiver and the coupler for blocking the first upstream light signals transmitted from the coupler.

4. The system according to claim 3, configured for obtaining a measurement of a dark spectrum with the dedicated shutter closed for adjusting a subsequent measurement of the upstream signal to improve signal-to-noise ratio using the measurement of the dark spectrum.

5. The system according to claim 1, comprising a receiver coupler coupled between the light receiver and the coupler for bundling upstream light signals from two or more couplers.

6. The system according to claim 5, wherein the receiver coupler includes a filter that is configured to attenuate one or more wavelengths provided by the light source and/or facilitate transmission of one or more monitoring signals.

7. The system according to claim 6, comprising a mode-mixing element for coupling the light receiver to the receiver coupler for homogenizing a signal provided to the light receiver from the filter.

8. The system according to claim 7, wherein the mode-mixing element is a non-circular light guide such as a square fiber, a hexagonal fiber, a square rod or a hexagonal rod.

9. The system according to claim 1, wherein the light receiver comprises a photodetector and/or a spectrometer and/or a combination of a wavelength de-multiplexing unit and one or more photodetectors.

10. The system according to claim 1, wherein the light source and the light receiver are communicatively connected to a signal processing unit for collecting, analyzing and processing data for further use.

11. The system according to claim 10 wherein the signal processing unit is communicatively connected to a remote data processing unit that collects the data from the treatment, analyses it and delivers guidance for the drug delivery.

12. The system according to claim 10 wherein the signal processing unit is configured for using algorithms based on machine learning and/or artificial intelligence for analyzing the data from one or more earlier treatments and delivers guidance for the drug delivery.

13. The system according to claim 1, wherein the coupler is a passive two-way fiber coupler.

* * * * *